United States Patent [19]

Sievers et al.

[11] Patent Number: 4,514,522

[45] Date of Patent: Apr. 30, 1985

[54] OXYGEN SORBENT

[75] Inventors: Robert E. Sievers; John N. Gillis, both of Boulder, Colo.

[73] Assignee: University Patents, Inc., Westport, Conn.

[21] Appl. No.: 635,320

[22] Filed: Jul. 27, 1984

[51] Int. Cl.³ .............................................. C08J 9/40
[52] U.S. Cl. ................................. 521/53; 521/153; 528/9; 528/396; 528/423
[58] Field of Search .......................................... 521/53

[56] References Cited

U.S. PATENT DOCUMENTS 4,198,792  4/1980  Frosch et al. ...................... 521/55

Primary Examiner—Morton Foelak
Attorney, Agent, or Firm—George M. Yahwak

[57] ABSTRACT

The present invention discloses a novel and unique family of agents which reversibly binds molecular oxygen at room temperature.

9 Claims, 5 Drawing Figures

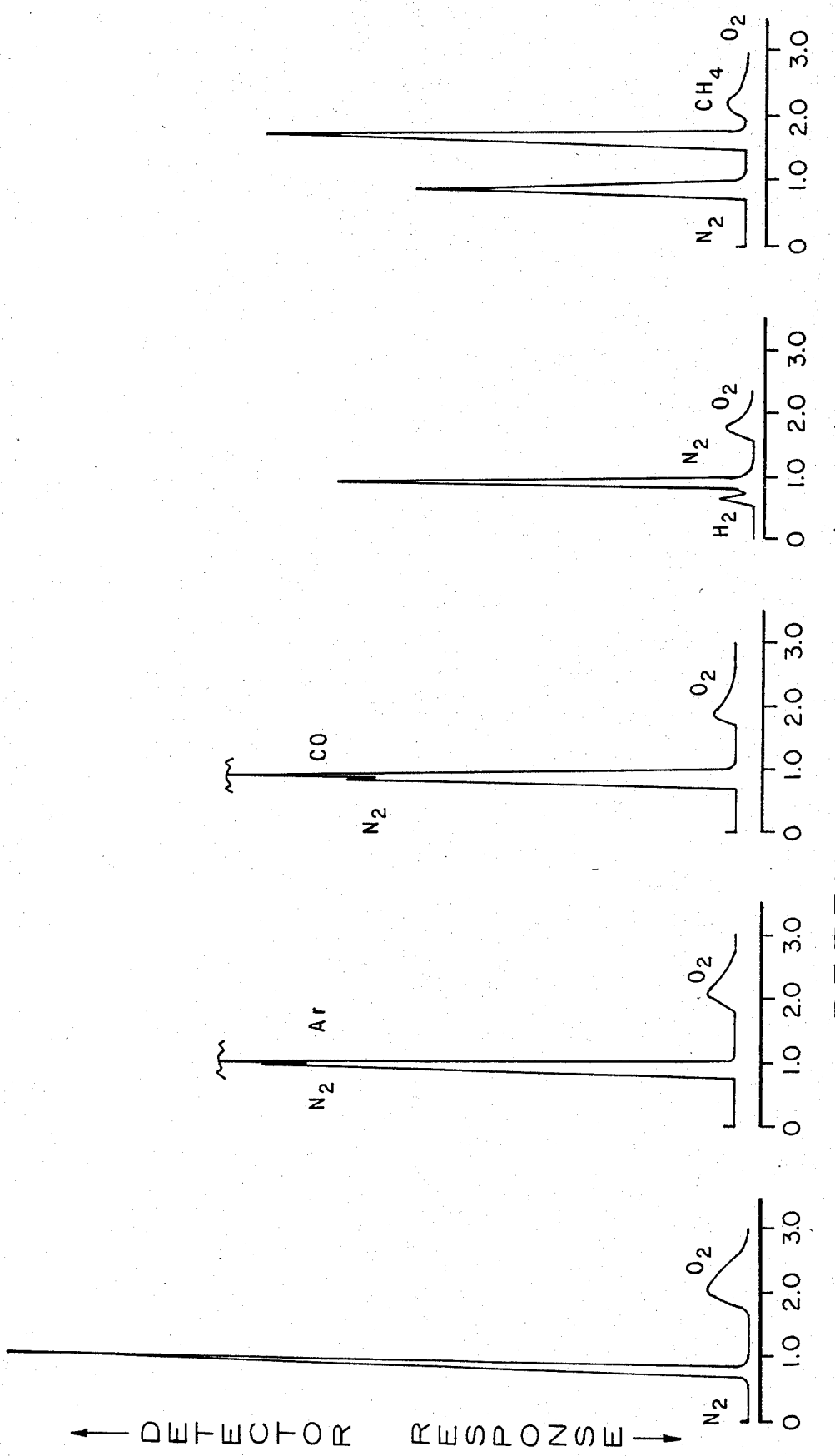

OXYGEN SORBENT

Partial funding for the present invention was obtained from the NASA-Ames Research Center, Moffett Field, Calif.

The separation of oxygen from mixed gases has both academic and industrial importance. The present invention discloses a novel and unique family of agents which reversibly binds molecular oxygen under ambient room temperature conditions.

A number of prior disclosures in the patent literature relate to the attempts to achieve oxygen separation. Descriptive of such disclosures are:

U.S. Pat. Nos. 2,450,276, 2,508,490, and 4,032,617 describe cobalt chelate compositions that are similar to each other but different from that of the present invention; the parent compound being described and the two related disclosures describe the use of substituted analogs of this compound to adsorb oxygen. In each case the cobalt chelate is used pure, in the solid state (not bonded in a polymer), to adsorb oxygen. These compounds are known to reversibly bind oxygen in the solid state in a 2:1 metal chelate to molecular oxygen ratio. The cobalt chelates used to synthesize Oxysorb (as we have named our metal chelates bonded to porous polymers) have varying degrees of stability toward molecular oxygen in their pure solid state. Reversible adsorption of oxygen by the pure compounds of the present invention has not been observed. The reversible adsorption of molecular oxygen is made possible because of the role of nitrogens in the polymer support activating the cobalt in the case of Oxysorb.

The disclosures in U.S. Pat. Nos. 3,230,045 and 4,343,715 use metal chelates that are similar or identical to hemoglobin or myoglobin, which transport and store oxygen in numerous biological systems. Unlike cobalt chelates of the present invention, these complexes contain iron as the metal ion, which binds directly to the oxygen molecule. The cobalt chelates used to synthesize Oxysorb are easy and inexpensive to produce, compared to those similar to biological molecules, and, in addition, have little or no affinity for carbon monoxide, which is known to adsorb strongly to hemoglobin or myoglobin.

The disclosure contained in U.S. Pat. No. 4,198,792, uses cobalt chelates imbedded into a cross-linked polymer matrix *not* containing an activating nitrogen functionality; a nitrogen base is added to promote the oxygen adsorbing property of the compounds. A disadvantage of their material relative to ours is that the nitrogen base, e.g., pyridine, is not bonded to the polymer and may be lost by volatilization. Our approach to the synthesis of Oxysorb was fundamentally different because we utilized a polymer that has incorporated into its structure a nitrogen that becomes an integral vital part of the overall structure of Oxysorb. This approach was used so that specific sites within the polymer matrix would anchor, isolate and activate the metal chelate, decreasing the possibility of irreversible oxygen adsorption.

In addition to the prior attempts to use metal chelates for the adsorption of oxygen, prior attempts have also been made to separate gases, including oxygen, by the use of various polymers. The porous polymers described in U.S. Pat. Nos. 3,357,158 and 3,486,298, for example, have been used to separate oxygen from nitrogen and/or argon at −78° C. Oxysorb has the capability of providing this separation under ambient room temperature conditions.

It is, accordingly, an object of the present invention to describe a family of agents which reversibly binds molecular oxygen under ambient room temperature conditions.

The broad aspects of the objects of the present invention are achieved by the use of metal chelates of Schiff bases which have been bonded to porous polymers which contain a nitrogen functionality required to activate the metal atom in the chelate molecule.

More specifically, the metal chelates of Schiff bases are compounds of the general formula:

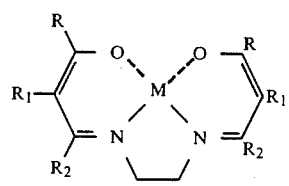

wherein M is the metal component, and R, $R_1$, and $R_2$ are selected from the group consisting of hydrogen, lower alkyl containing from 1 to 10 carbon atoms, and the perfluoro lower alkyl containing from 1 to 10 carbon atoms.

The term "lower alkyl containing from 1 to 10 carbon atoms" is meant to encompass methyl to decyl moieties and all isomeric forms of the alkyl as, for example, when the lower alkyl contains 4 carbon atoms the term is meant to encompass n-butyl, iso-butyl, sec-butyl, and t-butyl substituents. The term "polyfluoro-lower alkyl" indicates that hydrogen atoms in the alkyl moiety have been replaced by fluorine atoms, and is also meant to encompass perfluoro—lower alkyls wherein all hydrogens are substituted. The term "M" is meant to be limited to the preferred metallic component, cobalt, as well as to a broader class of metals having like utility in bonding Schiff base, for example, divalent metals such as iron, copper, manganese, nickel, zinc, palladium, and platinum, as well as the four valent compound, vanadium.

Although a number of these metal chelates have been previously reported, their bonding to a porous polymer containing nitrogen functionalities, and the disclosed utilities of these bonded chelates has not been reported.

The preferred metal chelate of a Schiff base is the chelate of the formula

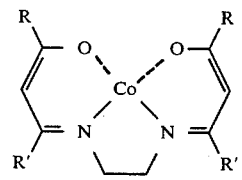

wherein R is t-butyl and R' is iso-butyl. More specifically, this chelate is [5,5'-(1,2-ethanediyldinitrilo)-bis(2,2,7-trimethyl-3-octanato)]cobalt (II). Conventionally this metal chelate is referred to as Co(toden).

This preferred metal chelate has not been previously reported, and being novel, is considered to be one aspect of the present invention.

The metal chelates of the present invention are prepared from "keto-amino"-type Schiff bases resulting from the condensation of β-diketone and 1,2-diaminoethane. These bases have the general formula:

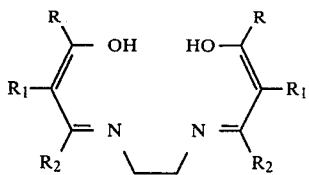

wherein R, $R_1$, and $R_2$ are as previously defined.

Although many of these "keto-amino"-type Schiff bases have been previously reported, the base which is an intermediate to the formation of the preferred metal chelate, Co(toden), has not been previously reported. Being novel, this intermediate is considered to be one aspect of the present invention. Specifically, this Schiff base has the formula:

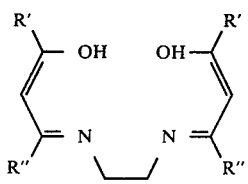

wherein R' is t-butyl, and R" is iso-butyl. More specifically, this Schiff base is 5,5'-(1,2-ethanediyldinitrilo)-bis(2,2,7-trimethyl-3-octanone). Conventionally, this Schiff base is referred to as $H_2$toden.

The following specific examples detailing the synthesis of the preferred compounds according to the present invention are offered by way of further illustration of the present invention. Although limited to the preferred compounds, the examples may readily be modified by those skilled in the art to incorporate those substituted compounds wherein "R" groups are other than the illustrated butyl-substituted compounds. Accordingly, the following examples are not meant to be limiting of the present invention.

EXAMPLE I

Absolute ethanol (1035 ml) was added to 306 grams of neopentanoic acid in a flask fitted with a heating mantle and a reflux condenser. To this mixture was slowly added 65 ml of concentrated sulfuric acid, and the mixture heated under reflux for three hours. Heating was discontinued and the hot mixture was extracted with 4 liters of a 10% sodium carbonate solution. The organic layer which separated was collected and dried overnight with magnesium sulfate. It was then filtered and purified by distillation at atmospheric pressure. A low heat was first applied in order to collect a fraction at a temperature of 73° C. consisting principally of ethanol. When the head temperature began to drop, the heat was raised and a second fraction, consisting of ethyl pivalate was collected.

A three-neck round-bottom flask was fitted with a reflux condenser with an attached drying tube containing calcium chloride, a dropping funnel, and a glass tube connected by Tygon tubing to a tank of nitrogen gas. During the reaction, the mixture was continually stirred by a magnetic stirring apparatus. Toluene (350 ml) which had been dried over Linde Molecular Sieve 4A, was then added to the flask. A gentle flow of nitrogen passed through a trap containing Linde Molecular Sieve 13X, was used to continually sweep out the system. Sodium hydride (67.2 grams of a 50% dispersion in mineral oil) was then added to the toluene, followed by 106.5 ml of ethyl pivalate. The MIBK (88 ml which had been dried over Linde Molecular Sieve 3A) was placed in the dropping funnel and, prior to addition, the mixture in the flask was heated to 96° C. in a boiling water bath. The addition was done dropwise over the course of three hours. Heat was continued for an additional half hour, after which the reaction was left stirring under nitrogen overnight. At this point, the mixture was a greenish-yellow color and no additional toluene was needed to keep the mixture stirring.

The next day the flask was packed in an ice bath and 260 ml of an 18% hydrochloric acid solution was slowly added. During the neutralization, the nitrogen flow was left on and stirring was done as vigorously as possible. The two resulting layers were filtered by suction filtration. The organic layer was then collected, and the toluene was removed by rotary evaporation. The resulting organic residue was made up largely of H(tod) (about 81% yield) of suitable purity to be used directly in subsequent synthesis of additional compounds.

EXAMPLE II

Preparation of 5,5'-(1,2-ethanediyldinitrilo)bis-2,2,7-trimethyl-3-octanone).

To a 250-ml round bottom flask was added 16.0 g $(8.7 \times 10^{-2}$ mole) of 2,2,7-trimethyl-3,5-octanedione(H-tod) in 20 ml of absolute methanol. To this solution was added 3.6 g $(6.0 \times 10^{-2}$ mole) of 1,2-diaminoethane in an equal volume of methanol. The addition was done dropwise with stirring at room temperature. The solution was stirred for two hours after the addition was complete then concentrated to an off-white liquid by rotary evaporation. The liquid was placed under vacuum (0.5 torr) and heated to 95° C. in a water bath. The resulting solid was recrystallized twice in dry acetone to yield 4.9 g (29%) of a white crystalline solid, mp 114°–115° C. Analysis: Calculated for $C_{24}H_{44}N_2O_2$: C, 73.42; H, 11.30; N, 7.14. Found: C, 73.04; H, 11.35; N, 7.15.

EXAMPLE III

Preparation of [5,5'-(1,2-ethanediyldinitrilo)bis(2,2,7-trimethyl-3-octanato)]cobalt (II).

A 100-ml flask was equipped with a magnetic stirrer, heating mantle and nitrogen inlet. To this flask was added 0.595 g $(2.5 \times 10^{-3}$ mole) of cobalt (II) chloride hexahydrate dissolved in 5 ml of water. Nitrogen flow (10 ml/min.) was started and 0.98 g $(2.5 \times 10^{-3}$ mole) of $H_2$toden (made in accordance with Example II) dissolved in 20 ml ethanol was slowly added; during the addition of the ligand a precipitate formed. The mixture was gently heated, with stirring, after the addition was complete until all of the solid was dissolved, producing a red/brown solution. To this solution was added 1 ml of 5N NaOH $(5.0 \times 10^{-3}$ mole), at which time the solution turned dark green and a precipitate formed. The mixture was heated until boiling and stirred at this temperature for 45 minutes. During this time an orange solid formed, which was isolated by filtration, then washed with about 25 ml of water. The solid was recrystallized in hexanes to yield 0.593 g (53%) of fine orange needles, mp 163°–165° C. Analysis: Calculated for $CoC_{24}H_{42}N_2O_2$: C,64.11; H,9.43; N,6.23. Found: C,63,54; H,9,30; N,6.65.

EXAMPLE IV

Preparation of the Porous Polymer

The porous polymer is prepared similar to the method of Hollis, modified by Pollock. A 250-ml 3-necked flask was equipped with a condenser, overhead stirrer and nitrogen inlet. The flask was placed in a temperature-controlled water bath. An aqueous solution consisting of 400 mg of hydroxypropyl methylcellulose gum dissolved in 90 ml of water and 4 ml of diethylbenzene, 300 mg of 2,2-azobis(2-methyl-propionitrile), 23.1 ml of diethylbenzene, 15.0 ml of ethylvinylbenzene and 4.5 ml of 4-vinylpyridine was prepared at) °C. Nitrogen flow (10 ml/min) was started over the stirred aqueous phase, and the organic solution was slowly added. The resulting white solution was heated with stirring to 55° C. over the next 1.5 hours and left to stir at 55° C. for an additional 6 hours. The temperature was then increased to 65° C. for 2 hours than 70° C. for about 12 hours. The resulting mixture was filtered to isolate the porous polymer beads, which were placed in 250 ml of water and stirred for about 30 minutes. This process was repeated 5 times, then repeated another 4 times using fresh aliquots (200 ml) of methanol as the solvent. The porous polymer was then extracted using a Soxhlet apparatus for at least 48 hours using acetone as the solvent. The solid was dried under vacuum (0.5 torr) for 12 hours at room temperature and 5 hours at 100° C. to yield 31.7 g (78%) of small (0.1 mm in diameter) white beads. The solid was kept in a sealed container until used.

EXAMPLE V

Preparation of Oxysorb; Method I

A 250-ml flask was equipped with a pressure equalizing addition funnel and a magnetic stirrer. To this flask was added 0.118 g ($3.00 \times 10^{-4}$ mole) of 5,5'-(1,2-ethaneidyldinitrilo)bis(2,2,7-trimethyl-3-octanone) dissolved in 40 ml of absolute methanol. To this stirred solution was added $7.52 \times 10^{-2}$ g ($3.00 \times 10^{-4}$ mole) of cobalt (II) acetate tetrahydrate dissolved in 10 ml of absolute methanol. The addition was made dropwise and at room temperature, and the solution turned dark green during the course of the addition. About 5 minutes after the addition was complete, 3.0 g of the porous polymer was added and the mixture was stirred at room temperature for 1 hour, during which time the solid turned brown and the solution became almost colorless. The solvent was removed by rotary evaporation to give a brown solid, which was washed with 50 ml of water then dried under vacuum (0.5 torr) at room temperature for 12 hours. The yield of Oxysorb is essentially quantitative.

Method II

To a solution of $4.5 \times 10^{-2}$ G ($1.0 \times 10^{-4}$ mole) of Co(toden) (made in accordance with Example III) dissolved in 10 ml of hexanes, was added 1.0 g of the porous polymer. The mixture was stirred for 5 min. at room temperature, then the solvent was removed by rotary evaporator to give a light yellow solid, which was then dried under vacuum (0.5 torr) at room temperature for about three hours. The light yellow solid turns brown upon exposure to air and the yellow color can be reinstated by placing the sample under vacuum for several seconds.

The experimental design used to demonstrate the utility of Oxysorb can be described as follows: A gas chromatograph was fitted with two packed columns. The first column, which was placed immediately following the injection port, was constructed of glass tubing 4 mm × 16 cm and contained about 700 mg of Oxysorb. Attached to this column (following in series) a second column to be used for the separation of other gases. This second column is not necessary if only retardation of the elution of $O_2$ relative to the other gases is desired. The second column consists of a 2 mm × 265 cm stainless steel column packed with 3.87 g of Porapak-N. No resolution of nitrogen and oxygen is observed using only this column without the Oxysorb column in series. The exit end of the Porapak-N column was connected to a thermal conductivity detector. The Porapak-N column and the Oxysorb column were connected using reducing union tube fittings constructed of stainless steel. This minimizes dead volume in the system and either column can be removed or changed in minutes. The injection port, analytical column and detector can be changed or modified for more diverse or more specific applications.

A number of chromatographic separations were conducted utilizing this design. The results of these separations can best be described by reference to the figures.

FIG. 1 demonstrates the separation of oxygen and nitrogen in ambient air streams. The chromatograph shown results from injecting about 3 $\mu l$ of ambient air into the designed system.

FIG. 2 shows the separation of oxygen from argon and nitrogen, the other two main constituents of air. The sample injected was 4-$\mu l$ in volume, consisting of about equal volumes of air and argon.

FIG. 3 shows the separation of oxygen from carbon monoxide and nitrogen. The volume of the sample injected was 4-$\mu l$ consisting of about equal volumes of air and carbon monoxide. The performance of Oxysorb does not appear to be affected by the injection of samples which contain carbon monoxide.

FIGS. 4 and 5 show the separation of oxygen in samples which contain other permanent gases that might be present in an industrial sample. The sample sizes injected are 4-$\mu l$. The FIG. 4 sample contains hydrogen, oxygen, and nitrogen, the FIG. 5 sample contains nitrogen, methane, and oxygen. The coupling of the column containing Oxysorb to the Porapak-N column had little or no effect on the retention time of the species other than oxygen, and the performance of the oxygen-sensitive column was unchanged after injection of these gases.

In addition to the metal chelate polymer-bonded Schiff base used to obtain the chromatographic separations depicted in FIGS. 1 to 5, other metal chelate polymer-bonded Schiff bases described by the general formulae according to the present invention. For example, the compound [2,2'-(1,2-ethanediylbis[nitrilomethylidyne])-bis(phenolato)]cobalt(II), and substituted analogs can act as oxygen carriers when bonded to the polymer described above. Baseline resolution of oxygen and nitrogen in elution chromatography systems can be achieved when these compounds are used in a manner similar to that described for the other organic ligands.

Oxysorb could be useful for several purposes. For example, the determination of oxygen and nitrogen in industrial oxygen is often necessary. At room temperature molecular sieves will separate nitrogen and oxygen, but argon, which can be an impurity in industrial grade oxygen, will co-elute with oxygen. The sequence of elution using molecular sieves is oxygen and argon followed by nitrogen. If nitrogen is at the ppm level the large oxygen peak could overlap the nitrogen peak, making quantification difficult or impossible. Modifications to the chromatographic system or low temperatures have been used to achieve this separation (a common modification uses a copper catalyst to convert the oxygen to water). Modifications and systems which must operate at other than ambient temperatures complicate the analysis considerably and make the separation more costly, both of which are undesirable for a routine method.

Oxysorb, when used as the stationary phase in a chromatographic system, allows baseline resolution of oxygen from nitrogen and argon. The elution order is nitrogen, argon, then oxygen, so large amounts of oxygen will not interfere with nitrogen or argon determination. The oxygen peak is also retained enough so that small amounts of oxygen could be detected in nitrogen or argon if desired. The separation is accomplished at room temperature within a few minutes time. Less than one gram of Oxysorb packed in a chromatographic column and attached in series with the desired analytical column results in better than baseline resolution of oxygen and nitrogen in a 5-$\mu$l sample of air. Since the column is selective for oxygen, other species present can be separated using the usual stationary phase with little or no interference from the addition of the column containing Oxysorb.

Another possible use of Oxysorb would be as an adsorbent for use in a device which would separate oxygen from air, resulting in oxygen of high purity. This type of apparatus has numerous industrial as well as medical applications. Many devices of this type have been described and many use molecular sieves as the adsorbent bed and a pressure or temperature swing to remove the nitrogen adsorbed from air. A device of this type, using molecular sieves would also concentrate argon in air (1% by volume) to about 5% by volume in the resulting oxygen because oxygen and argon are not separated on an adsorbent bed of molecular sieves. Such a device using Oxysorb as the adsorbent, would eliminate argon from the purified oxygen. The device using Oxysorb as the adsorbent would also be inherently more efficient because the desired species, which constitutes about 20% of air by volume, is trapped, then removed, rather than trapping about 80% ($N_2$) of the total flow to recover a species present in 20% ($O_2$) of the flow.

The approach the present invention utilizes to separate oxygen from air is unique. The separation has most often been accomplished using molecular sieves or materials which separate these species on the basis of molecular size or their different rates of diffusion through a certain medium. Our approach uses the selective interaction of the Oxysorb with molecular oxygen to achieve this separation.

Thus, while we have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview, of the following claims.

Having thus described our invention and the manner and process of making and using it, in such full, clear, concise, and exact terms so as to enable any person skilled in the art to which it pertains, or with which it is most nearly connected, to make and use the same;

We claim:

1. A metallic complex of a Schiff base of the general formula

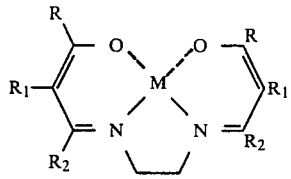

wherein R, $R_1$ and $R_2$ are selected from the group consisting of hydrogen, lower alkyl containing from 1 to 10 carbon atoms, and polyfluoromoieties containing from 1 to 10 carbon atoms bonded to a porous synthetic organic polymer containing a nitrogen functionality.

2. A metallic complex of claim 1 wherein M is selected from the group consisting of iron, copper, cobalt, manganese, nickel, zinc, palladium, platinum, and vanadium.

3. The metallic complex of claim 2 wherein M is cobalt.

4. The metallic complex of claim 2 wherein the polymer comprises vinylpyridine monomer.

5. The metallic complex of claim 4 wherein the polymer further comprises diethylbenzene and ethylvinylbenzene monomers.

6. The bonded complex of claim 1 wherein the nitrogen functionality is a pyridyl group.

7. The bonded complex of claim 1 wherein the nitrogen functionality is an exocyclic nitrogen moiety.

8. The bonded complex of claim 1 wherein $R_1$ is the cobalt complex of a Schiff base is hydrogen.

9. The bonded complex of claim 5 wherein R is t-butyl, and $R_2$ is iso-butyl.

* * * * *